United States Patent [19]

Winterton et al.

[11] Patent Number: 5,209,865

[45] Date of Patent: May 11, 1993

[54] CONDITIONING SOLUTION FOR CONTACT LENSES AND A METHOD OF USING THE SAME

[75] Inventors: Lynn C. Winterton, Roswell; Kai C. Su, Alpharetta, both of Ga.

[73] Assignee: Ciba-Geigy Corporation, Ardsley, N.Y.

[21] Appl. No.: 470,105

[22] Filed: Jan. 25, 1990

[51] Int. Cl.$^5$ .............................................. C11D 1/44
[52] U.S. Cl. ............................... 252/174.22; 252/106; 252/DIG. 1; 252/DIG. 14; 134/22.19
[58] Field of Search ............ 252/174.22, 106, DIG. 14, 252/DIG. 1; 134/22.19

[56] References Cited

U.S. PATENT DOCUMENTS

| | | | |
|---|---|---|---|
| 3,882,036 | 5/1975 | Krezanoski et al. | 252/106 |
| 3,954,644 | 5/1976 | Krezanoski et al. | 252/106 |
| 4,323,467 | 4/1982 | Fu | 252/106 |
| 4,440,662 | 4/1984 | Tsuzuki et al. | 252/106 |
| 4,734,222 | 3/1988 | Winterton et al. | 252/174.22 |
| 4,820,352 | 4/1989 | Riedhammer et al. | 252/173 |

OTHER PUBLICATIONS

CT JA International Cosmetic Ingredient Dictionary, pp. 448–449, 451–454 4th Ed., 1991.
The Merck Index, Encyclopedia, 11th ed, p. 7541, 1989.

Primary Examiner—Mark L. Bell
Assistant Examiner—C. M. Bonner
Attorney, Agent, or Firm—Wenderoth, Lind & Ponack

[57] ABSTRACT

A contact lens conditioning solution which has a polyoxyethylene-polyoxypropylene substituted ethylenediamine nonionic surfactant (Poloxamine type) having a hydrophile-lipophile balance of seven or below and a carrier vehicle. A polyoxyethylene-polyoxypropylene nonionic surfactant (Poloxamer type) having a hydraulic-lipophile balance of seven or below and a polyoxyethylene concentration of less than about 20% by weight of the polyoxyethylene-polyoxypropylene nonionic surfactant may also be included in the solution.

14 Claims, 3 Drawing Sheets

CONDITIONING SOLUTION FOR CONTACT LENSES AND A METHOD OF USING THE SAME

BACKGROUND OF THE INVENTION

The present invention relates to an improved contact lens conditioning solution. More particularly, it relates to a solution which renders the contact lens surface more wettable so that proteins, lipids and other tear film substituents do not adhere and form deposits on the lens surface.

Contact lenses are typically made of plastic and, therefore, are hydrophobic or water repellant. Since the use of the first contact lenses, there has been a recognized need to use conditioning agents for contact lenses to render the contact lenses more hydrophilic or "wettable". The purpose of these conditioning agents is to render the lens surface more wettable so that proteins, lipids, and other tear film substituents do not adhere and form deposits thereon. Such deposits reduce the comfort and safety of the lens, and also interfere with optical clarity since it is important that the tear fluid spread evenly over the surface of the lens.

Hard contact lenses, such as those fabricated from poly (methylmethacrylate), are of such firmness that contamination can be removed by mechanical means, such as by rubbing a lens soaked in cleaning solution between one's fingers. However, soft contact lenses, such as those fabricated from hydrophilic materials, such as 2-hydroxyethyl methacrylate (HEMA), and some rigid gas permeable (RGP) material lenses, require greater care in removing deposits since cleaning solutions can be absorbed and concentrated in the lens and because the soft lenses are more apt to tear or suffer other damage during mechanical cleaning.

Presently, an enzymatic cleaner consisting of a proteolyic enzyme, such as papain, which is effective in removing protenatious deposits from the contact lens surface, is relied upon to provide a clean lens. The enzyme is typically provided in a kit with vials, into which are placed enzyme tablets. The tablets are dissolved in saline, distilled water or 3% peroxide, and the lenses are typically soaked from between 2 to 6 hours. Following enzymatic cleaning, it is necessary to disinfect the contact lens. A problem exists, however, in that the use of enzymes is expensive and can be quite inconvenient.

Therefore, there exists a need for a conditioning solution which renders a contact lens surface more wettable so that proteins, lipids and other tear film substituents do not adhere thereto and form deposits. There is a further need for such a solution which may be used on hard, RGP and hydrogel (soft) contact lenses. Such a conditioning solution would greatly enhance the cleaning operations now required.

SUMMARY OF THE INVENTION

Figure 1:
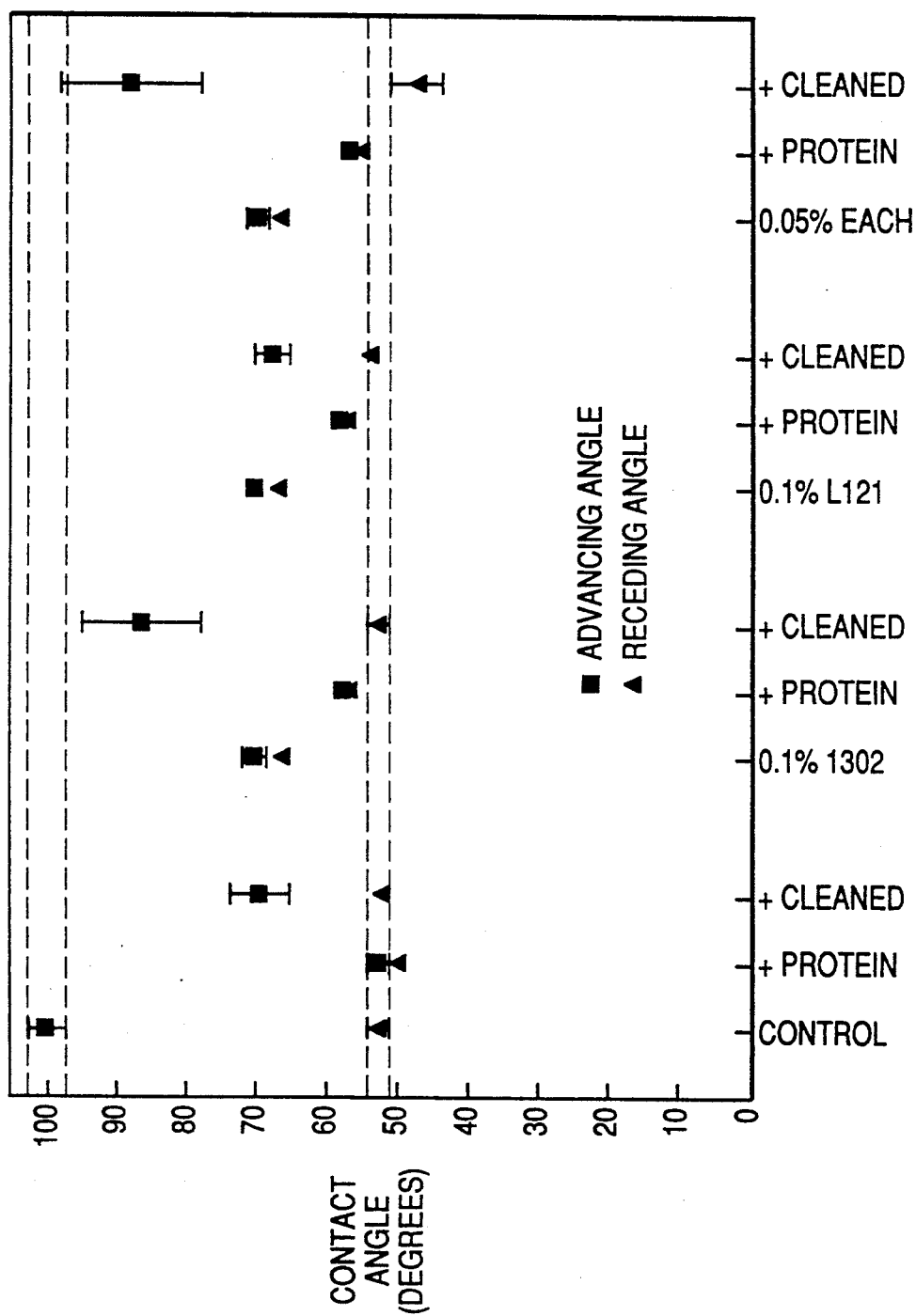
FIG. 1 summarizes the results of an experiment in which an RGP lens was conditioned according to the present invention.

The present invention relates to a conditioning solution for contact lenses which comprises a polyoxyethylene-polyoxypropylene substituted ethylenediamine nonionic surfactant having a hydrophile-lipophile balance of seven or below and having a molecular weight of between about 3,600 and about 9,000. Such surfactants are typically known generally as "Poloxamine", and sold under the trademark "Tetronics" ® (BASF-Wyandotte).

The solution may also have a polyoxyethylene-polyoxypropylene nonionic surfactant having a hydrophile-lipophile balance of seven or below and a polyoxyethylene concentration of less than about 20% by weight. Such surfactants are generally known as "Poloxamers" and sold under the trademark "Pluronics" ® (BASF-Wyandotte), and typically have a molecular weight of between and about 2,000 and about 5,000.

The solution according to the present invention forms a uniform hydrophilic film on a lens surface for which proteins and lipids have very little affinity. As such, a contact lens contacted by the solution will have a coating which provides a prophylactic effect to the lens.

It is, therefore, an object of the present invention to provide a conditioning solution which renders a contact lens surface more wettable so that proteins, lipids and other tear film substituents do not adhere thereto and form deposits.

It is a further object of the present invention to provide for such a solution which may be used on hard, RGP and soft contact lenses.

DETAILED DESCRIPTION OF THE PREFERRED EMBODIMENTS

The present invention provides a prophylactic action in preventing and/or retarding tear film deposits on the surfaces of contact lenses. The ingredients form a uniform hydrophilic film on the lens surface for which proteins and lipids have very little affinity. Furthermore, although some minor amounts of tear film substituents may adhere to the film, the protective film can be sacrificially removed, along with any adherence, by digitally cleaning the contact lens with any appropriate contact lens cleaner. The removal of the sacrificial film is virtually complete so that the contact lens is "renewed" to its native clean state. It is envisioned that the present solution may be used separately from other ophthalmic solutions, or may also be incorporated into a cleaning, conditioning or disinfecting solution, thus aiding in compliance with existing protocols rather than adding an extra solution, product or care step to achieve the desired prophylactic results.

The conditioning solution for contact lenses according to the present invention comprises a polyoxyethylene-polyoxypropylene substituted ethylenediamine nonionic surfactant having a hydrophile-lipophile balance of seven or below and, may contain a polyoxyethylene-polyoxypropylene nonionic surfactant having a hydrophile-lipophile balance of seven or below and a polyoxyethylene concentration of less than about 20% by weight.

The polyoxyethylene-polyoxypropylene substituted ethylenediamine nonionic surfactant and the polyoxyethylene-polyoxypropylene nonionic surfactant are both surface active agents which have as low a hydrophile-lipophile balance (HLB) as will be tolerated in the formulations. The low HLB value in the surface active agent indicate a high affinity for hydrophobic (lipophilic) surfaces. These surfaces active agents strongly adhere to those hydrophobic regions of the contact lens and render them hydrophilic. This adherence forms a "barrier" to potential absorbance, and keeps them from the surface of the lens. Furthermore, this increase in hydrophilicity simultaneously decreases the thermodynamic driving force for protein and lipid absorption, thereby retarding tear film deposits.

The polyoxyethylene-polyoxypropylene substituted ethylenediamine nonionic surfactant is more commonly known as a "TETRONIC®" type surfactant. (Tetronic® is a trademark of BASF-Wyandotte Corp.) The Tetronic® type surfactant is a tetra-functional block copolymer derived from the sequential addition of propylene oxide and ethylene oxide to ethylenediamine, and is represented by the following structure:

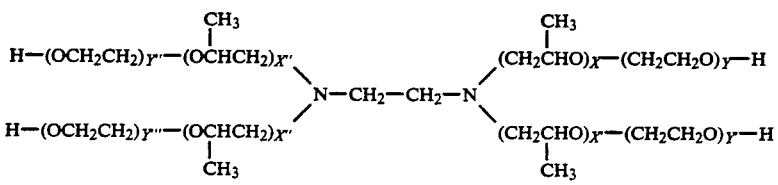

The Tetronic® type surfactant is also known by the generic name "poloxamine" and is commercially available from BASF-Wyandotte Corp. Their preparation can be found in U.S. Pat. No. 2,979,528, which is incorporated herein by reference. For convenience purposes, the polyoxyethylene-polypropylene substituted ethylenediamine nonionic surfactant will be identified generally as "Tetronic®", with a numeral suffix to identify a particular grade of material as available from BASF-Wyandotte Corp.

It has been discovered that only tetronics having a hydrophile-lipophile balance of seven or below are suitable for use in the conditioning solution of the present invention. Such tetronics typically have the molecular weight of between about 3,600 and about 9,000 and include Tetronic 701; 702; 901; 1101; 1102; 1301; 1302; 1501; and 1502 from BASF-Wyandotte known as poloxamer 701, 702, 901, 1101, 1102, 1301, 1302, 1501 and 1502 respectively.

The polyoxyethylene-polyoxypropylene nonionic surfactant is sold under the trademark "PLURONIC®" by BASF-Wyandotte Corp., and comprises a series of closely related block polymers that may generally be classified as polyoxyethylene-polyoxypropylene condensates terminating in primary hydroxyl groups. They are formed by the condensation of propylene oxide onto a propylene glyconucleous followed by the condensation of ethylene oxide onto both ends of the polyoxypropylene base. The polyoxyethyl hydrophilic groups on the ends of the molecule are controlling length to constitute anywhere from 10% to 80% by weight of the final molecule. The structure of the polyethylene-polyoxypropylene nonionic surfactant is preferably as follows:

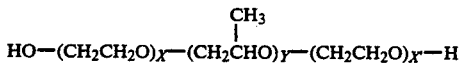

For convenience purposes, the polyoxyethylene-polyoxypropylene nonionic surfactant will be referred to herein as Pluronic® generally, with a numerical suffix to identify a particular grade of material as available from BASF-Wyandotte Corp.

It has been discovered that the polyoxyethylene-polyoxypropylene nonionic surfactant useful in the present invention must have a HLB of seven or below and a polyoxyethylene concentration of less than about 20% by weight. Such preferred surfactants include Pluronic L61, L81, L101, and L121 from BASF-Wyandotte Corp. or poloxamer 181, 321, 331, and 401, respectively. These polyoxyethylene-polyoxypropylene nonionic surfactants have a molecular weight of between about 2,000 and about 5,000.

The polyoxyethylene-polyoxypropylene substituted ethylenediamine nonionic surfactant may be present in an amount up to 1% by volume of the solution, and preferably at approximately 0.6%. Furthermore, the polyoxyethylene-polyoxypropylene nonionic surfactant may be present in an amount up to about 1.0% by weight of the solution, with the preferred amount being approximately 0.2% by volume.

The conditioning solution is ocularly compatible and may be used on hard, RGP, and soft contact lenses. The active ingredients may be in any of a number of carrier vehicles. For example, the solution may be used in a soaking conditioning solution with or without a preservative or disinfecting agent.

To prevent agglomeration of oils on a lens in the eye, as is common among patients who wear make-up, an ocularly compatible surfactant, preferably having an HLB higher than about 7, may be added to the solution. For example, polysorbate 60, polysorbate 80, poloxymer F127 or poloxymer F107 may be used for this purpose. The lens could be soaked in the solution to allow the active ingredients to absorb to the lens surface and/or the internal matrix. Alternatively, the solution may be placed in an eye drop solution, which may also be dispensed with or without a preservative or disinfecting agent. The drop would be applied to the lens while being worn on the eye. Furthermore, the conditioning solution may be placed within a contact lens cleaning solution, which would deliver the active ingredients while the lens is being cleaned. In this type of formulation, the active ingredient would not be used to clean, and other detergent agents should also be provided.

The following examples are provided to illustrate the invention in a number of carrier vehicles. In each example, the ingredients (each numerical value represents percent by weight in 100 cc of an aqueous solution) were put in purified water, thoroughly mixed and stirred and dissolved to form an aqueous solution. The pH of the solution was adjusted to an ocularly acceptable level to obtain the desired composition.

EXAMPLE I

Disinfectant a) 30.0 mg/ml hydrogen peroxide (31% solution)
b) Hydrogen peroxide stabilizer (such as sodium stannate)
c) Buffering salts
d) 0.06 mg/ml poloxamine 1302 (Tetronic ®)
e) 0.04 mg/ml polysorbate 80 (Tween 80)
f) Purified water, q.s. 100%

EXAMPLE II

Disinfectant a) 30.0 mg/ml hydrogen peroxide (31% solution)
b) Hydrogen peroxide stabilizer (such as sodium stannate)
c) 0.01 mg/ml poloxamine 1302 (Tetronic ®)
d) 0.003 mg/ml poloxamer 401 (Pluronic ®)
e) Purified water, q.s. 100%

EXAMPLE III

Disinfectant a) 30.0 mg/ml hydrogen peroxide (31% solution)
b) Hydrogen peroxide stabilizer (such as sodium stannate)
c) 0.01 mg/ml poloxamine 1302 (Tetronic ®)
d) Purified water, q.s. 100%

EXAMPLE IV

Disinfectant Neutralizer a) Buffering salts
b) 0.002 mg/ml disodium EDTA
c) 0.06 mg/ml poloxamine 1302 (Tetronic ®)
d) 0.04 mg/ml polysorbate 80
e) 0.001 mg/ml sorbic acid
f) NaCl to adjust osmolarity to isotonicity
g) Catalase enzyme (700,000 activity units/L)
h) Purified water, q.s. 100%

EXAMPLE V

Disinfectant Neutralizer a) Buffering salts
b) 0.002 mg/ml disodium EDTA
c) 0.01 mg/ml poloxamine 1302 (Tetronic ®)
d) 0.001 mg/ml sorbic acid
d) NaCl to adjust osmolarity to isotonicity
f) Catalase enzyme (700,000 activity units/L)
g) Purified water, q.s. 100%

EXAMPLE VI

Disinfectant Neutralizer a) Buffering salts
b) 0.01 mg/ml poloxamine 1302 (Tetronic ®)
c) 0.003 mg/ml poloxamer 401 (Pluronic ®)
d) NaCl to adjust osmolarity to isotonicity
e) Catalase enzyme (700,000 activity units/L)
g) Purified water, q.s. 100%

EXAMPLE VII

Preserved Saline or Eye Drops a) Buffering salts
b) 0.001 mg/ml disodium EDTA
c) 0.01 mg/ml poloxamine 1302 (Tetronic ®)
d) 0.003 mg/ml poloxamer 401 (Pluronic ®)
e) 0.0025 mg/ml sorbic acid
f) NaCl to adjust osmolarity to isotonicity (if desired)
g) Purified water, q.s. 100%

EXAMPLE VIII

Unpreserved Saline or Eye Drops II a) Buffering salts
b) 0.01 mg/ml poloxamine 1302 (Tetronic ®)
c) 0.003 mg/ml poloxamer 401 (Pluronic ®)
d) NaCl to adjust osmolarity to isotonicity (if desired)
g) Purified water, q.s. 100%

EXAMPLE IX

Preserved Saline or Eye Drops a) Buffering salts
b) 0.001 mg/ml disodium EDTA (if desired)
c) 0.01 mg/ml poloxamine 1302 (Tetronic ®)
d) 0.0025 mg/ml sorbic acid (if desired)
e) NaCl to adjust osmolarity to isotonicity (if desired)
g) Purified water, q.s. 100%

EXAMPLE X

Preserved Saline or Eye Drops a) Buffering salts
b) 0.001 mg/ml disodium EDTA
c) 0.01 mg/ml poloxamine 1302 (Tetronic ®)
d) 0.003 mg/ml poloxamer 401 (Pluronic ®)
e) Mixture of methyl and propyl parabens
f) NaCl to adjust osmolarity to isotonicity (if desired)
g) Purified water, q.s. 100%

Figure 2:
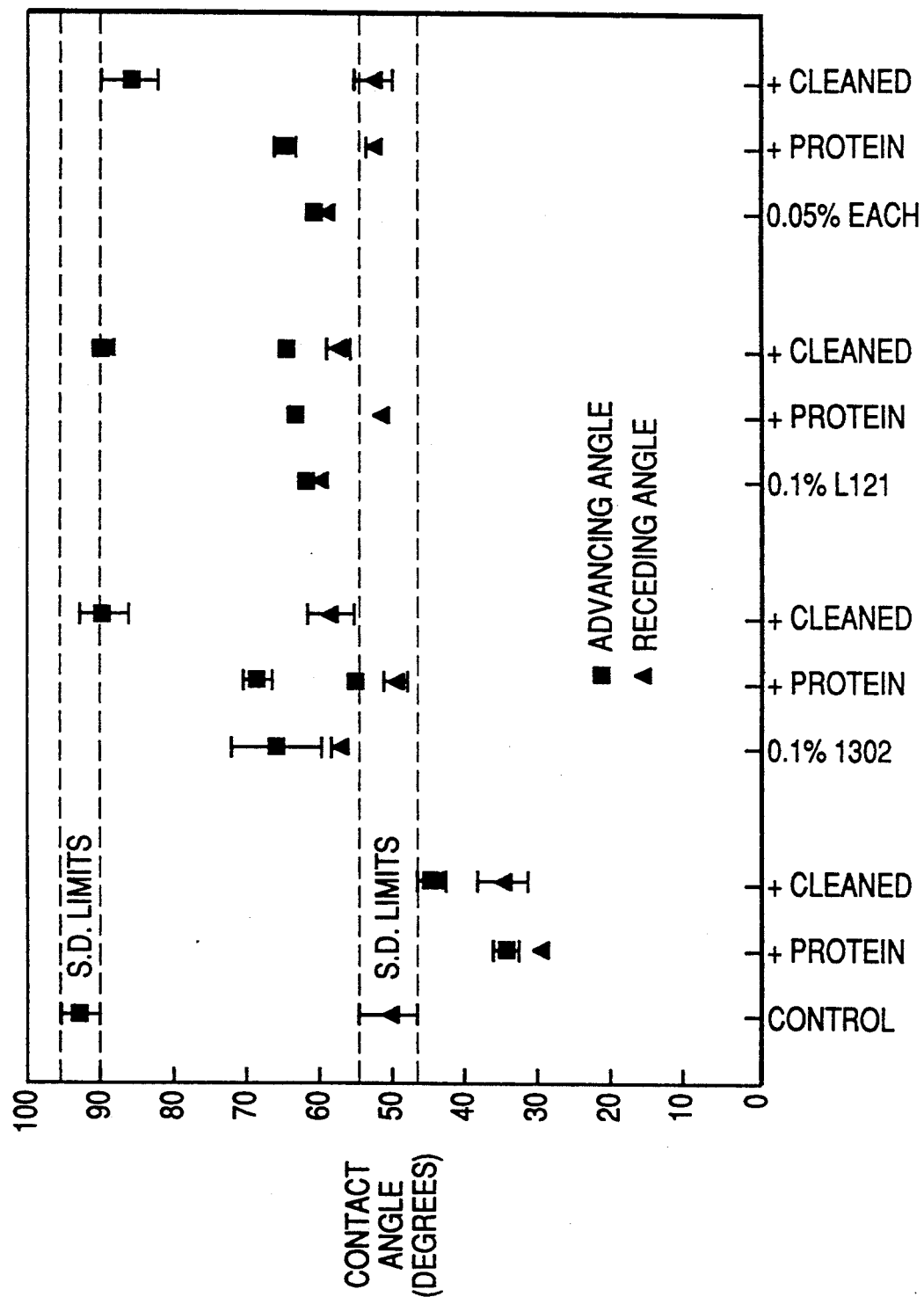
FIG. 2 summarizes the results of an experiment in which a PMMA lens was conditioned according to the present invention.
Figure 3:
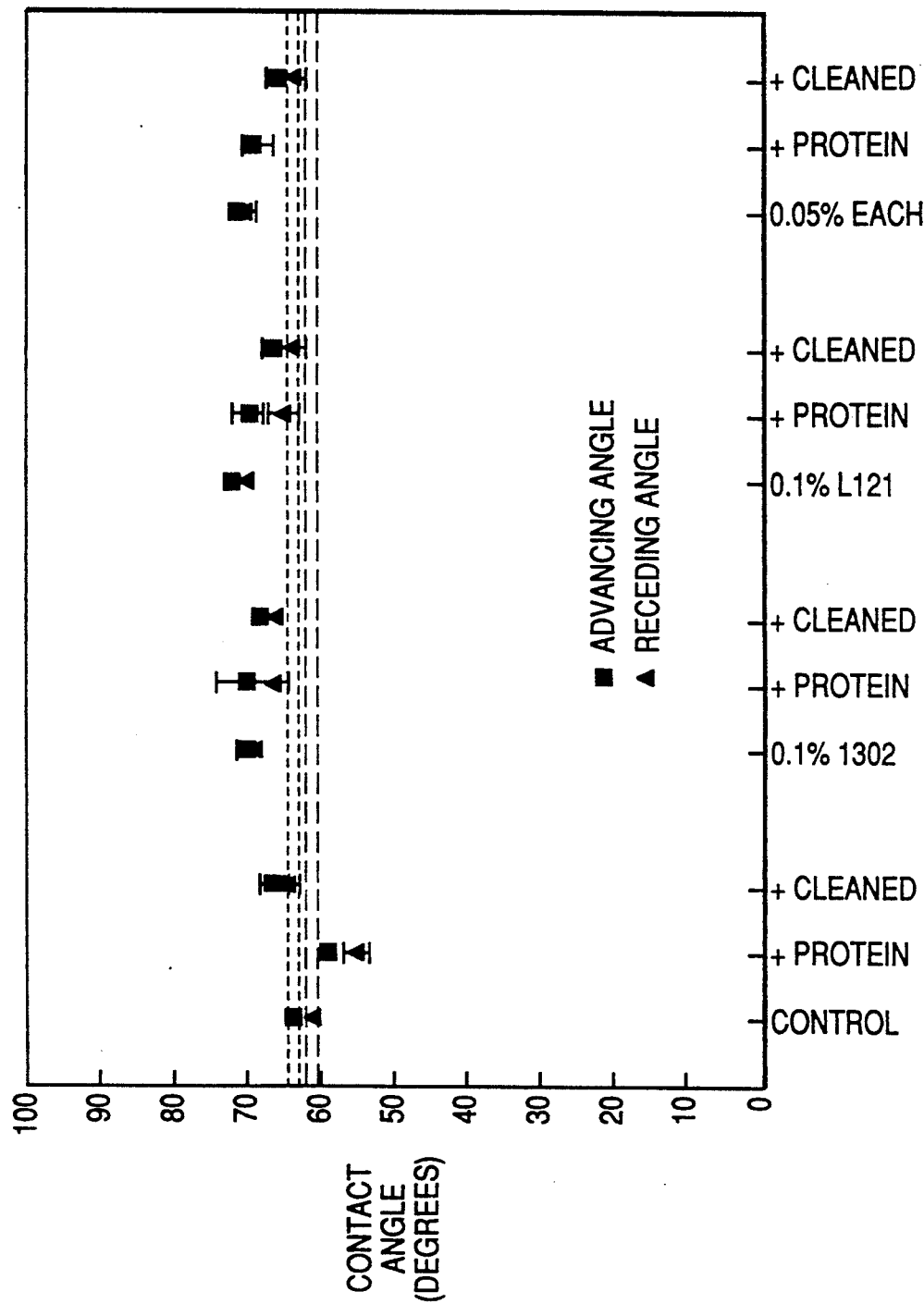
FIG. 3 summarizes the results of an experiment in which a HEMA lens was conditioned according to the present invention.

The efficacy of the improved conditioning solution of the present invention was determined in a series of tests, the results of which are set forth in FIGS. 1, 2 and 3. Contact angle is the angle between a liquid surface and a solid surface and is an indication of the relative values of the force of adhesion and cohesion. The advancing angle is the contact angle achieved when additional liquid is placed onto the solid and the receiving angle is the contact angle resulting when liquid is removed from the solid. A contact angle of 0. implies complete wetting of the solid by the liquid and a contact angle of 180 indicates absolute non-wetting.

In the present test, the efficacy of the conditioning solution of the present invention was found by measuring the contact angles of the solution on samples of various contact lens material and comparing the angle to those of cleaned samples of the same material. The proximity of the advancing and receiving angles of the conditioned and cleaned lenses to its respective control is an indication of the efficacy of the conditioning solution to prevent protein build-up of the material.

Prior to analysis, the lens materials were cleaned with a contact lens daily cleaner, rinsed thoroughly with ultrapure H$_2$O and placed inside an ultrasonic cleaner containing a 2% Micro TM Cleaning Solution. The materials were rubbed gently on both sides with sterile cotton balls to remove any residual deposits and then left in the ultrasonic bath for at least 15 minutes. The materials were then rinsed with ultrapure water, recleaned with the cleaner and again rinsed thoroughly with ultrapure water. A minimum of three (3) sample materials for each solution was used.

Contact angles (advancing and receding angles) were on each cleaned material before placing into artificial tears. The material coated with the protein were left to soak in the Solution of the present invention for 15 minutes prior to being placed in the artificial tear solution. All materials are then put inside a temperature controlled oven set at 37.C for a minimum of 8 hours. Contact Angles were performed on each material after treating with the protein. The materials were then cleaned with the cleaner and thoroughly rinsed with ultrapure $H_2O$ before final contact angles were determined.

As can be seen in FIG. 1, an RGP control group had an advancing angle of approximately 100° and a receiving angle of approximately 52°, accounting for standard derivations. Following addition of the protein but no conditioning solution and subsequent cleaning with a cleaning solution, the control group showed an advancing angle of approximately 70 and a receding angle of approximately 50. A second RGP group was then conditioned with a 0.1% conditioning solution of Tetronic® type 1302 and then immersed in the protein solution. Following cleaning, the advancing angle of the group closely approximated the range of the advancing angle of the control group, while the receiving angle was within the control group range. A third RGP group was conditioned with 0.1% Pluronic® type L121, immersed in protein, and subsequently cleaned. The results showed that the advancing angle was far from the control range and the receiving angle was within the control range. A fourth RGP group was conditioned with a solution of 0.05% each of Tetronic® type 1302 and Pluronic® type L121 and immersed in protein solution. Following cleaning, both the advancing angle and receiving angle were found to be within the range of the control.

A similar test, the results of which are summarized in FIG. 2, was conducted with a PMMA group. The test indicated that lens material conditioned in 0.1% Tetronic® type 1302, immersed in protein and subsequently cleaned exhibited an advancing angle in the o control and a receiving angle closely approximating the o control. A second PMMA group conditioned in 0.1% Pluronic® type L121 exhibited an advancing angle within the control but a receding angle outside the control range. A third PMMA group conditioned with a 0.5% solution of each of Tetronic®type 1302 and Pluronic® type L212 and subsequently cleaned exhibited both in advancing angle and a receiving angle within the control ranges.

A similar study as above was conducted with a HEMA type group, and is summarized in FIG. 3. The study showed that a 0.1% conditioning solution of Tetronic® type 1302 resulted in an advancing angle and receiving angle both closely approximating the control. A conditioning solution of 0.1% Pluronic® type L121 conditioning solution resulted in a receding angle within the control but an advancing angle outside of the control. A conditioning solution containing 0.05% each of Tetronic® type 1302 and Pluronic® type L121 exhibited both an advancing angle and a receiving angle within the control.

Therefore, it was found that in each case, the Tetronic® 1302 afforded results approximating the control, and the mixture of the Tetronice and Pluronic® achieved the goal of meeting the control characteristics. The use of Pluronice alone was unacceptable. It can be said that lens material conditioned according to the present invention will be more wettable, and hence can be cleaned more easily, than such material otherwise conditioned.

What is claimed is:

1. A contact lens conditioning solution which comprises a carrier vehicle and as active ingredients (a) an effective amount of up to about 1.0% (weight/volume) of a polyoxyethylene-polyoxypropylene substituted ethylenediamine nonionic surfactant (poloxamine type) having a hydrophile-lipophile balance of seven or below and having a polyoxyethylene concentration between about 10% and about 20% by weight and (b) an effective amount of up to about 1.0% (weight/volume) of a polyoxyethylene-polyoxypropylene nonionic surfactant (poloxamer type) having a hydrophile-lipophile balance of seven or below and a polyoxyethylene concentration of less than about 20% by weight of said polyoxypropylene-polyoxyethylene nonionic surfactant.

2. The solution of claim 1, wherein said polyoxyethylene-polyoxypropylene substituted ethylenediamine nonionic surfactant has a molecular weight between about 3600 and about 9000.

3. The solution of claim 1, wherein said effective amount of said polyoxyethylene-polyoxypropylene substituted ethylenediamine nonionic surfactant is about 0.6% (weight/volume) of said solution.

4. The solution of claim 1, wherein said polyoxyethylene-polyoxypropylene nonionic surfactant has a molecular weight between about 2000 and about 5000.

5. The solution of claim 1, wherein said effective amount of said polyoxyethylene-polyoxypropylene nonionic surfactant is about 0.2% (weight/volume) of said solution.

6. The solution of claim 1 and further comprising an effective amount of a preservative.

7. The solution of claim 1 and further comprising an effective amount of a disinfectant.

8. The solution of claim 1, wherein said polyoxyethylene-polyoxypropylene substituted ethylenediamine nonionic surfactant is selected from the group consisting of polomaxine 701, poloxamine 702, poloxamine 901, poloxamine 1101, poloxamine 1102, poloxamine 1301, poloxamine 1302, poloxamine 1501 and poloxamine 1502.

9. The solution of claim 1, wherein said polyoxyethylene-polyoxypropylene nonionic surfactant is selected from the group consisting of poloxamer 181, poloxamer 321, poloxamer 331 and poloxamer 401.

10. The solution of claim 1 wherein the disinfectant is hydrogen peroxide.

11. A method for conditioning a contact lens, comprising the step of contacting said lens with a solution comprising a carrier vehicle having (a) an effective amount of up to about 1.0% (weight/volume) of a polyoxyethylene-polyoxypropylene substituted ethylenediamine nonionic surfactant having a hydrophile-lipophile balance of seven or below and having a polyoxyethylene concentration between about 10% and about 20% by weight and (b) an effective amount of up to about 1.0% (weight/volume) of a polyoxyethylene-polyoxypropylene nonionic surfactant having a hydrophile-lipophile balance of seven or below and a polyoxyethylene concentration of less than about 20% by weight of said polyoxypropylene-polyoxyethylene nonionic surfactant.

12. The method of claim 11, wherein said polyoxyethylene-polyoxypropylene substituted ethylenediamine nonionic surfactant has a molecular weight between about 3600 and about 9000.

13. The method of claim 11, wherein said polyoxyethylene-polyoxypropylene nonionic surfactant has a molecular weight between about 2000 and about 5000.

14. The method of claim 11, wherein said effective amount of a polyoxyethylene-polyoxypropylene nonionic surfactant is about 0.6% (weight/volume) of said solution.

* * * * *